United States Patent [19]

Smith et al.

[11] Patent Number: 4,559,157

[45] Date of Patent: Dec. 17, 1985

[54] COSMETIC APPLICATOR USEFUL FOR SKIN MOISTURIZING

[75] Inventors: James A. Smith, Old Tappan; James E. Reilly, Wanaque, both of N.J.

[73] Assignee: Creative Products Resource Associates, Ltd., Clifton, N.J.

[21] Appl. No.: 487,252

[22] Filed: Apr. 21, 1983

[51] Int. Cl.$^4$ .............................................. B05D 3/02
[52] U.S. Cl. ................................. 252/90; 252/91; 424/27; 424/28; 427/27; 427/28; 15/104.92; 15/104.93; 106/8; 106/9; 428/320.2
[58] Field of Search ................. 424/27, 28; 252/90, 252/91; 427/27, 28; 15/104.92, 104.93; 106/8, 9

[56] References Cited

U.S. PATENT DOCUMENTS

| | | | |
|---|---|---|---|
| 1,687,625 | 10/1928 | MacKenzie | 15/104.93 |
| 3,057,467 | 10/1962 | Williams | 206/46 |
| 3,283,357 | 11/1966 | Decker et al. | 424/27 |
| 3,414,927 | 12/1968 | Worcester | 15/104.93 |
| 3,691,270 | 9/1972 | Charle et al. | 15/104.93 X |
| 3,795,624 | 3/1974 | Feinstone | 15/104.93 X |
| 3,881,210 | 5/1975 | Drach et al. | 252/90 X |
| 3,939,260 | 2/1976 | Lafon | 424/28 |
| 3,965,518 | 6/1976 | Muoio | 15/104.93 |
| 4,075,375 | 2/1978 | Komatsu | 15/104.93 X |
| 4,112,167 | 9/1978 | Dake et al. | 428/159 X |
| 4,206,195 | 6/1980 | Bolich, Jr. et al. | 15/104.93 X |

FOREIGN PATENT DOCUMENTS 2402730  7/1975  Fed. Rep. of Germany ... 15/104.93

Primary Examiner—George F. Lesmes
Assistant Examiner—Nancy A. B. Swisher
Attorney, Agent, or Firm—Kenyon & Kenyon

[57] ABSTRACT

The present invention relates to cosmetic applicators comprising absorbent sheets impregnated with an oil-in-water emulsion incorporating various emollients which are particularly adapted for moisturizing wet skin surfaces.

10 Claims, No Drawings

COSMETIC APPLICATOR USEFUL FOR SKIN MOISTURIZING

BACKGROUND OF THE INVENTION

The present invention relates to cosmetic applicators comprising absorbent sheets impregnated with an oil-in-water emulsion incorporating various emollients which are useful for moisturizing skin surfaces and which are particularly adapted for moisturizing wet skin surfaces.

A variety of treated cloths which are adapted for skin washing and cleansing are commercially available. Such products comprise paper or fabric sheets which are wetted with an aqueous solution of a water-soluble lanolin derivative, detergents, and polyhydric alcohols. These solutions may also contain large amounts of denatured alcohol which function to dry the skin soon after their exposure to air so that the sheets may perform both a cleansing and a drying function. One typical solution of the alcohol-water type is disclosed in U.S. Pat. No. 3,057,467. These compositions are compatible with moistened skin, but are not capable of delivering the large amounts of emollients required for effective moisturizing.

Oil-based emollient liquids, on the other hand, possess sufficient moisturizing power but are incompatible with wet skin in that the emollient oils tend to clump and spread unevenly when applied thereto.

It is, therefore, an object of the present invention to provide a cosmetic applicator which will function to effectively moisturize skin, particularly wetted skin, when it is pressed or rubbed against the skin.

It is another object of the present invention to provide a cosmetic applicator which is adapted for multiple whole-body moisturizations.

Other objects, advantages and novel features of the present invention will be apparent to those skilled in the art from the following description and appended claims.

BRIEF DESCRIPTION OF THE INVENTION

The objects of the present invention are attained by providing a cosmetic applicator comprising a sheet of absorbent material which is impregnated with an oil-in-water emulsion comprising an oil phase containing at least one emollient oil and at least one emollient wax stabilizer dispersed in an aqueous phase comprising at least one polyhydric alcohol emollient and at least one organic water-soluble detergent. Effective amounts of bactericidal preservatives and fragrance may also be employed in the impregnating emulsion. The emulsions of the present invention are formulated so that an effective amount of emollients and fragrance is released and evenly coated onto the skin with no "skipping" or separation when the impregnated sheet is pressed or rubbed against a moist skin surface. This requires that the emulsion be formulated so that it will be stable and not break when mixed with the additional water present on the skin due to bathing, showering or the like.

It has been found that emollient emulsions stable under these conditions can be formulated by dispersing an oil phase comprising one or more emollient oils and one or more emollient wax stabilizers in an aqueous phase comprising one or more polyhydric alcohol emollients and one or more water-soluble organic detergents. Both the oil phase and the aqueous phase may also incorporate bactericidal stabilizers in combined amounts effective to prevent bacterial and fungal growth in the applicators during storage or after they have been wetted by use. The emulsions of the present invention may also incorporate an effective amount of a fragrance.

Therefore, the emulsions of the present invention preferably will comprise about 15-50% of water-insoluble or soluble active ingredients, i.e., the emollients, detergents, fragrance and preservatives; and 50-85% water, preferably distilled or deionized water. About 7-20% of the active ingredients will be present as the oil phase of the emulsion, while the remainder of the active ingredients will be fully-soluble in the water phase. Emollients will preferably comprise about 10-50% by weight of the emulsions. Emollients useful in the practice of the present invention are generally described by G. Barnet, Emollient Creams and Lotions, and by S. J. Strianze, Hand Creams and Lotions, in *Cosmetics—Science and Technology*, Wiley Interscience Pub. (1957) at pages 99–181.

DETAILED DESCRIPTION OF THE INVENTION

The emulsions useful in the present invention are formulated from an oil phase which incorporates one or more emollient oils, which are preferably present in an amount equal to about 4-12% by weight of the entire emulsion.

Emollient oils generally function to lubricate the skin surface and to prevent evaporative loss of skin moisture supplied by underlying tissues. They also function to provide a protective barrier against environmental irritants. The emollient oils useful in the practice of the present invention include those commonly employed in emollient creams and lotions, such as liquid hydrocarbons (petrolatum, mineral oil, and the like) vegetable and animal fats and oils (lanolin and its derivatives, cholesterol and its derivatives, phytosterols, and the like), alkyl fatty acid esters (methyl, isopropyl, and butyl esters of fatty acids, and the like), fatty alcohol esters of benzoic acids and $C_4$-$C_6$ alkanoic acids, phospholipids and their derivatives (lecithin, cephalin and the like) and silicones. In the practice of the present invention, mineral oils are preferred and may consist of one or more of the commercially available white mineral oils such as Carnation ® white mineral oil available from Witco Chemical Corp., Petrolia, Pa. (Viscosity at 40° C.: 10.8–13.6 cst, S.G. at 25° C.: 0.829–0.845). Preferably, the mineral oil will be present at about 2-7% by weight of the emulsions of the present invention.

Another preferred class of emollient oil useful in the emulsions of the present invention is the $C_{12}$-$C_{18}$ fatty alcohol esters of $C_4$-$C_6$ alkanoic acids, which may comprise about 2-4% by weight of the emulsion. An especially preferred member of this class of emollient oil is isostearyl neopentanoate, which is commercially available from Van Dyk and Co., Belleville, N.J. as Ceraphyll ® 375.

Another class of emollient oils useful in the practice of the present invention is the phytosterols such as the polyethoxylated soya sterol Generol ® 122 series which is commercially available from General Mills, Minneapolis, Minnesota. Generol ® 122-E-10 and 122-E-16 are especially preferred as components of the present emulsions. They are primarily mixtures of sitosterol and campersterol in which the C-3hydroxyl groups have been derivatized with a chain of about 10 or 16 ethanoloxy groups, respectively. The phytosterols are used as a minor component of the emulsions of the present invention, usually less than 1%.

Emollient wax stabilizers function to soften and smooth the skin surface and to prevent evaporation of interior skin moisture. They also function as nonionic emulsifying agents and act to adjust to final viscosity of the composition. The emollient wax stabilizers useful in the practice of the present invention include beeswax, spermaceti, solid hydrocarbons, $C_{12}$-$C_{18}$ fatty alcohols, glyceryl monostearate, ethylene glycol monostearate, polyethylene glycol distearate and other $C_{12}$-$C_{18}$ fatty acid-$C_2$-$C_5$ polyol esters. Particularly useful in the practice of the present invention are the fatty alcohols, such as lauryl, cetyl, oleyl and stearyl alcohols or mixtures thereof, and the fatty acid-polyol esters, i.e., glyceryl monostearate, which is commercially available as Cerasynt ® Q from Van Dyk & Co., Belleville, N.J. In one class of emulsions useful in the practice of the present invention, all or a part of the Ceraphyll ® 375 is replaced with one of the emollient waxes of the Softisan ® Series (Dynamit Nobel Chemicals, Rockleigh, N.J.), a fragrant emollient ester of the class of compounds designated as triglycerides of $C_{10}$-$C_{18}$ saturated fatty acids, which allows the use of less fragrance, thus resulting in a cost savings. An especially useful member of this series is Softisan ® 100. Preferably, emollient waxes will make up about 3-10% of the composition, most preferably about 3.5-8%.

The emulsions of the present invention will also include one or more polyhydric alcohol emollients which are preferably $C_2$-$C_5$ alkanols substituted with 2-4 hydroxyl groups, such as propylene glycol, glycerol, and sorbitol. Polyhydric alcohol emollients will preferably make up 5-15% by weight of the emulsion. One especially preferred mixture of polyhydric alcohol emollients is an about 1:1 mixture of propylene glycol and glycerol.

The emulsions of the present invention will also include at least one, and preferably two, water-soluble organic detergents, which function primarily as emulsifying agents and which must be selected so as to permit the emulsions to spread evenly on wet skin without interfering with the action of the emollients. Water-soluble organic detergents useful in the practice of the present invention are generally described in British Pat. No. 1,429,143. One class of detergents useful in the formulation of the emulsions of the present invention is the $C_{14}$-$C_{18}$ primary alkyl sulfates, such as sodium lauryl sulfate, sodium cetyl sulfate, and sodium stearyl sulfate. Another preferred class of organic detergent is the trialkyl amine oxides wherein one alkyl group contains from about 0-28 carbon atoms, from 0 to about 2 hydroxy groups and from 0 to about 5 ether or amido linkages, there being at least one moiety which is an alkyl group containing from about 10 to about 18 carbon atoms and no ether linkages, and each of the other two alkyl groups is selected from the group consisting of alkyl groups and hydroxyalkyl or aminoalkyl groups containing from 1 to about 3 carbon atoms. Preferred amine oxides include lauryl(dimethyl)amine oxide which is available as a 29-31% aqueous solution from Onyx Chemical Co., Jersey City, N.J. as Ammonyx ® LO; or as a 30% aqueous solution of a 70-30 mixture of lauryl- and myristyl(dimethyl)amine oxide (Bio-Surf ® PBC-460, Biolab, Decatur, Ga.); coco-amido-propyl(-dimethyl)amine oxide, bis-2-aminoethyl(mixed coco)amine oxide, (dimethyl)- myristylamine oxide, stearyl(-dimethyl)amine oxide, and tallow(bishydroxyethyl)amine oxide. Preferably, the detergents will be present at about 0.5-10% by weight of the emulsion most preferably at 1-5% by weight of the emulsion.

The emulsions of the present invention will also include at least one antibactericidal preservative, most preferably one or more such preservatives will be included in both the oil and the water phase in a combined amount effective to prevent fungal and bacterial growth on the applicators both during storage before use and when moistened, and between applications. An especially preferred class of preservatives is the parabens family, the $C_1$-$C_4$ lower alkyl- or benzyl-esters of p-hydroxy-benzoic acids which also act to stabilize the emulsions. Another preferred preservative for use in the emulsions of the present invention is an aqueous solution of 5-chloro-2-methyl-4-isothiazolin-3-one which is commercially available as a 10-11% aqueous solution in combination with 3-4% 2-methyl-1-isothiazolin-3-one under the trade name Kathon ® CG concentrate from Rohm and Haas Co., Philadelphia, Pa. Preferably, the preservatives will make up about 0.05-1.0% by weight of the emulsion.

The emulsions of the present invention may also include a minor, i.e., 0.5-5% by weight, but effective amount of fragrance, which may be any of the commercially available perfumes which are compatible with the other emulsion ingredients. Representative, suitable fragrances are disclosed by S. J. Strianse in *Cosmetics—Science and Technology* at pages 169-171.

Therefore, preferred emulsions useful in the present invention may be formulated so as to contain about 50-85% water, about 4-12% emollient oil, about 3.0-10% emollient wax stabilizer, about 5-20% polyhydric alcohol emollient, about 0.5-10% organic, water-soluble detergent, about 0.025-0.75% antibacterial preservative and about 0.1 to 0.5% fragrance.

The emulsions of the present invention are generally prepared by melting together the emollient wax stabilizers, emollient oils and a part of the preservatives with stirring or shaking at temperatures in the range of about 75°-85° C. in order to prepare the oil phase of the emulsion. The hot oil phase is then added with vigorous agitation to the aqueous phase which has been separately prepared by dissolving the polyhydric alcohol emollients, a part of the preservatives, and a portion of the detergents, i.e., the alkyl dimethyl amine oxide, in water and heating the resultant solution to the same temperature as the oil phase. After a brief period of stirring, the resultant 65°-75° C. pre-emulsion is stabilized by the subsurface addition of the remainder of the detergent, i.e., the sodium lauryl sulfate, in a small portion of 20°-30° C. water. The emulsion is stirred and cooled to about 40°-50° C., at which point the neat fragrance is added. The mixture is stirred and cooled to below 40° C., and the remainder of the preservative is added in a small portion of water. The finished emulsions exhibit viscosities in the range of 1300-2000 cps.

The finished emulsion is then applied to the desired weight onto one or both sides of an absorbent sheet which may be formed from any woven or nonwoven fiber, fiber mixture or foam of sufficient wet strength and absorbency to hold an effective moisturing amount of the emulsion. Preferred nonwoven sheets are those formed from a 70-75/25-30 polyester/rayon blend such as the 70/30 polyester rayon blend available from Crown Textile Co., Philadelphia, Pa. (C-785, 1.25 oz.-/yd$^2$) or the 70/30 polyester/rayon blend available from Sterns and Foster, Cincinnati, Ohio (2005-8) or from Crown Textile Co. (PS-1500, 1.34 oz./yd²). To form an applicator adequate for one whole-body application, about 8–10 g of emulsion is applied to one 1.7–2.5 g, 8"×9.5" sheet of fabric, whereas 15–17 g of emulsion per sheet is applied in order to prepare an applicator suitable for 2–3 whole-body applications. In such preferred applications the emulsion comprises about 300–600% and about 600–1000% based on the weight of the porous sheet, respectively.

Any method of fabric or foam coating known in the art may be employed. For example, the emulsion may be coated onto a fabric or paper sheet by means of a Meyer Rod, a floating knife or doctor blade or may be rolled onto a foam sheet via a stainless steel roller, or applied by spraying.

After coating, the individual applicators may be folded into stacks and packaged in any of the moisture and vapor impermeable packages known in the art, such as those disclosed by U.S. Pat. Nos. 4,017,002; 3,325,003; 3,836,045; and 3,057,467, the disclosures of which are incorporated by reference herein.

The invention will be further described with reference to the following detailed examples.

EXAMPLE I

Normal Skin Moisturizing Formulation

The following ingredients were combined in the weight percentages indicated in Table I to form a moisturizing composition by the procedure described below.

TABLE I

| INGREDIENT | PERCENT | GRAMS |
|---|---|---|
| GROUP A | | |
| Glyceryl Monostearate | 5.0 | 750.0 |
| Cetyl Alcohol | 0.5 | 75.0 |
| Mineral Oil | 5.0 | 750.0 |
| i-Stearyl Neopentanoate | 3.0 | 450.0 |
| Propyl Parabens | 0.10 | 15.0 |
| Butyl Parabens | 0.05 | 7.5 |
| GROUP B | | |
| Water (deionized) | 62.15 | 9,322.5 |
| Methyl Parabens | 0.30 | 45.0 |
| Propylene Glycol | 5.00 | 750.0 |
| Glycerol | 5.00 | 750.0 |
| Lauryl Dimethyl Amine Oxide (29–31% Solution in H₂O) | 3.0 | 450.0 |
| GROUP C | | |
| Water | 5.0 | 750.0 |
| Sodium Lauryl Sulfate | 0.50 | 75.0 |
| Fragrance (P. Robertet 44954) | 0.30 | 45.0 |
| Water | 5.0 | 750.0 |
| Kathon CG (Preservative) | 0.10 | 15.0 |
| | 100.00 | 15,000.0 |

The oil-phase ingredients of Group A were mixed and heated to 75° C. The water-phase Group B ingredients were separately mixed, heated to 75° C. and then the Group A ingredients were added with good agitation. Stirring was contained for 10 minutes and a 23° C. solution of the Group C ingredients was added subsurface to the stirred 72° C. mixture. The emulsion was stirred and cooled to 45° C. at which point the fragrance was added. The mixture was stirred until its temperature fell to 35° C. The mixture was allowed to stand overnight and then the preservative solution was added with stirring. The mixture was stirred for 45 minutes and then 9.0 g was spread onto a 8"×9.5" sheet of Crown Textile C-785 (1.25 oz./yd²) via a Meyer Rod to form a one-use cosmetic applicator.

It was found that an emulsion load of 16.0 g could be applied to and retained in one C-785 sheet. An applicator prepared in this matter was found to be effective for at least two whole-body moisturizing applications.

The resultant applicators were moist but not sticky or unduly wet to the touch and readily applied a clear, non-sticky, homogenous film of the emollient emulsion to dry skin surfaces. The film retained these desirable characteristics when the skin was moistened prior to use of the applicator.

EXAMPLE II

Stabilizer Modifications

The formulation of Example I was modified to replace 0.05% of the glyceryl monostearate with 0.05% of either Generol 122-E-10 or Generol 122-E-16 in Group A. The formulations were both prepared as in Example I except that the Group A ingredients were added to the Group B ingredients at 80° C. and the Group C ingredients were subsurface added to the mixture at 73° C. These two formulations were coated onto fabric sheets as described in Example I to form applicators which also performed satisfactorily on wet and dry skin.

EXAMPLE III

Dry Skin Moisturizers

The formulation of Example I was modified to replace the Group A oil phase with each of the two phases listed below on Table II. Modifications of the preparation parameters from those of Example I are also given on Table II.

TABLE II

| | PERCENT | |
|---|---|---|
| INGREDIENT | III A (%) | III B (%) |
| Generol 122-E-10 | 0.30 | 0.10 |
| Glyceryl Monostearate | 4.70 | 4.90 |
| Cetyl Alcohol | 0.50 | 0.50 |
| Mineral Oil | 6.00 | 6.00 |
| Softisan 100 | 2.00 | 1.43 |
| Ceraphyl 375 | — | 0.57 |
| Propyl Parabens | 0.10 | 0.10 |
| Butyl Parabens | 0.05 | 0.05 |
| A into B | 78° C. | 76° C. |
| C Added at Batch Temp. | 68° C. | 70° C. |
| Kathon Soln. Added at Batch Temp. | 38° C. | 25° C. |

When applied to fabric squares by the procedure of Ex. I, the formulations of Exs. IIIA and IIIB also provide effective cosmetic applicators which contain an increased amount of emollient wax.

While certain representative embodiments of the invention have been described herein for purposes of illustration, it will be apparent to those skilled in the art that modifications therein may be made without departing from the spirit and scope of the invention.

What is claimed:

1. A cosmetic applicator comprising a porous sheet impregnated with an oil-in-water emulsion comprising an oil phase comprising at least one emollient oil and at least one emollient nonionic wax stabilizer dispersed in an aqueous phase comprising at least one polyhydric alcohol emollient, and at least one organic water-soluble detergent, said emulsion being adapted to evenly coat an effective moisturizing amount of emollients on a wet skin surface when said applicator is contacted with said skin under conditions of pressure wherein the emulsion comprises about 50–85% water, about 4–12% emollient oil, about 3.0–10% emollient nonionic wax stabilizer, 5–20% polyhydric alcohol emollient and about 0.5–10% detergent.

2. The cosmetic applicator of claim 1 wherein the emollient wax stabilizer is selected from the group consisting of polyol fatty acid esters, fatty alcohols or mixtures thereof, and the emollient oil is selected from the group consisting of mineral oil or a fatty acid ester of a $C_1$–$C_6$ alkyl alcohol or mixtures thereof.

3. The cosmetic applicator of claim 2 wherein the water-soluble detergent is selected from the group consisting of $C_{14}$–$C_{18}$ primary alkyl sulfates, $C_{10}$–$C_{28}$ alkyl (dimethyl)amine oxides, $C_{10}$–$C_{28}$ alkyl(bis-2-aminoethyl) amine oxides, $C_{10}$–$C_{28}$ alkyl(bis-2-hydroxyethyl)amine oxides, cocoamido-propyl(dimethyl)amine oxide and mixtures thereof.

4. The cosmetic applicator of claim 1 wherein the emulsion further comprises fragrance and at least one bactericidal preservative.

5. The cosmetic applicator of claim 4 wherein the bactericidal preservatives comprise at least one $C_1$–$C_4$ lower alkyl 4-hydroxybenzoate preservative.

6. The cosmetic applicator of claim 1 wherein the porous sheet is a sheet of nonwoven textile consisting of a mixture of hydrophobic and hydrophillic fibers.

7. The cosmetic applicator of claim 6 wherein the nonwoven textile sheet is formed from a blend of polyester and rayon fibers in a ratio of about 70–75:25–30 and wherein the weight ratio of said emulsion to said sheet is about 3–6:1.

8. The cosmetic applicator of claim 6 wherein the nonwoven textile sheet is formed from a blend of polyester and rayon fibers in a ratio of about 70–75:25–30 and wherein the weight ratio of said emulsion to said sheet is about 6–10:1.

9. The cosmetic applicator of claim 1 wherein the emulsion further comprises about 0.05–1.0% of a plurality of bactericidal preservatives and 0.05–5.0% fragrance.

10. The cosmetic applicator of claim 9 wherein the emulsion comprises about 50–85% water, about 3.5–8% of a mixture of glyceryl monostearate and cetyl alcohol, about 4–12% of a mixture of mineral oil and isostearyl neopentanoate, about 5–15% of a mixture of propylene glycol and glycerol and about 1–10% of a mixture of $C_{10}$–$C_{28}$ alkyl (dimethyl) amine oxide and sodium lauryl sulfate.

* * * * *